United States Patent [19]

Verbeek

[11] Patent Number: 5,672,169
[45] Date of Patent: Sep. 30, 1997

US005672169A

[54] STENT MOUNTING DEVICE

[75] Inventor: Marcel A. E. Verbeek, Geleen, Netherlands

[73] Assignee: Medtronic, Inc., Minneapolis, Minn.

[21] Appl. No.: 630,183

[22] Filed: Apr. 10, 1996

[51] Int. Cl.⁶ ................................................ A61B 17/00
[52] U.S. Cl. ........................ 606/1; 606/192; 623/1
[58] Field of Search ........................ 606/108, 194, 606/195, 198, 1, 151; 623/1, 12

[56] References Cited

U.S. PATENT DOCUMENTS

| | | | |
|---|---|---|---|
| 4,726,369 | 2/1988 | Mar | 606/1 |
| 4,800,882 | 1/1989 | Gianturco | 606/194 |
| 5,026,377 | 6/1991 | Burton et al. | 606/108 |
| 5,108,416 | 4/1992 | Ryan et al. | 606/194 |
| 5,147,302 | 9/1992 | Euteneuer et al. | 606/194 |
| 5,158,548 | 10/1992 | Lau et al. | 604/96 |
| 5,190,058 | 3/1993 | Jones et al. | 128/898 |
| 5,192,297 | 3/1993 | Hull | 606/195 |
| 5,201,757 | 4/1993 | Heyn et al. | 606/198 |
| 5,226,889 | 7/1993 | Sheiban | 604/101 |
| 5,242,399 | 9/1993 | Lau et al. | 604/104 |
| 5,266,073 | 11/1993 | Wall | 623/1 |
| 5,304,340 | 4/1994 | Downey | 606/194 |
| 5,306,294 | 4/1994 | Winston et al. | 623/1 |
| 5,328,469 | 7/1994 | Coletti | 606/194 |
| 5,338,296 | 8/1994 | Dalessandro et al. | 604/96 |
| 5,344,426 | 9/1994 | Lau et al. | 606/198 |
| 5,360,401 | 11/1994 | Turnland | 604/96 |
| 5,368,566 | 11/1994 | Crocker | 604/101 |
| 5,387,235 | 2/1995 | Chuter | 623/1 |
| 5,391,172 | 2/1995 | Williams et al. | 606/108 |
| 5,460,592 | 10/1995 | Langton et al. | 600/7 |

OTHER PUBLICATIONS

Rupp, et al., Patent Application "Stent Mounting and Transfer Device and Method", filed Dec. 21, 1995, USSN 08/576,720.

*Primary Examiner*—Robert A. Hafer
*Assistant Examiner*—Justine R. Yu
*Attorney, Agent, or Firm*—John R. Duncan; Dianne M. F. Plunkett; Harold R. Patton

[57] ABSTRACT

A stent mounting device and method of using the device comprising a disposable device for holding a stent, into which a delivery system such as a balloon catheter can be inserted, and the stent crimped onto the delivery system, after which the delivery system and mounted stent are removed from the device. A stent is carried in a channel formed by four corner segments of four co-axillay arranged spaced blocks. Two adjacent blocks are elastically mounted in each of two parallel, opposed, cooperating actuators. The corner segments form an elongated channel sized to retain a conventional stent. Two elastic rods are placed between opposite blocks in opposite actuators. When the actuators are pressed together the rods are deformed to provide pressure transverse to the line of pressure, so that the cross sectional area of the channel is decreased in both directions, crimping the stent uniformly onto a delivery system.

12 Claims, 2 Drawing Sheets

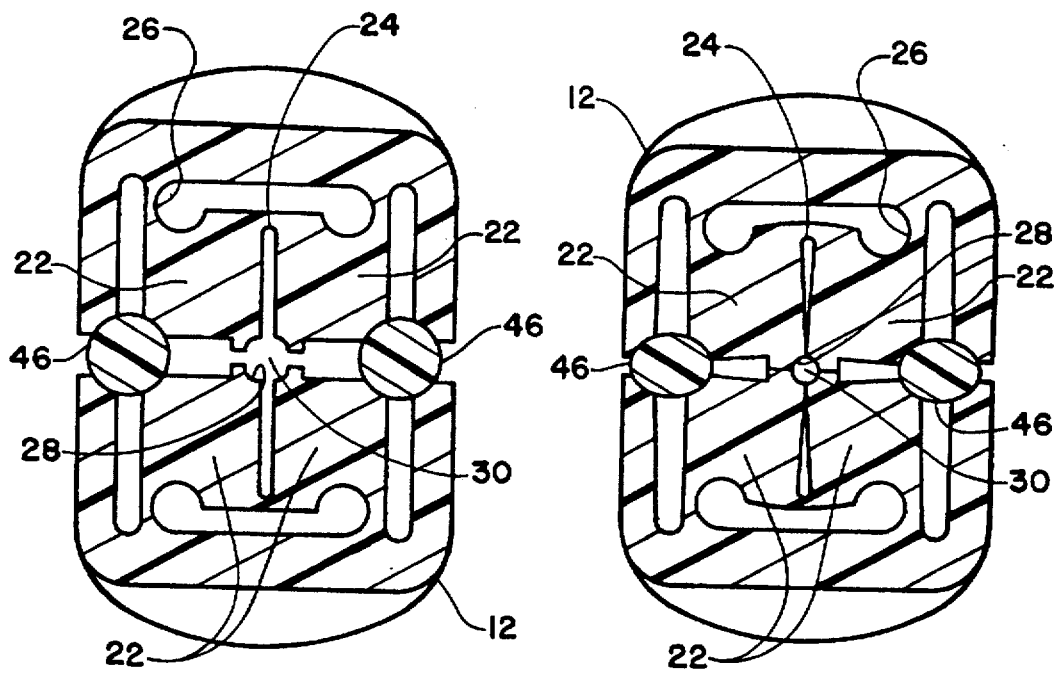
FIGURE 3
FIGURE 4
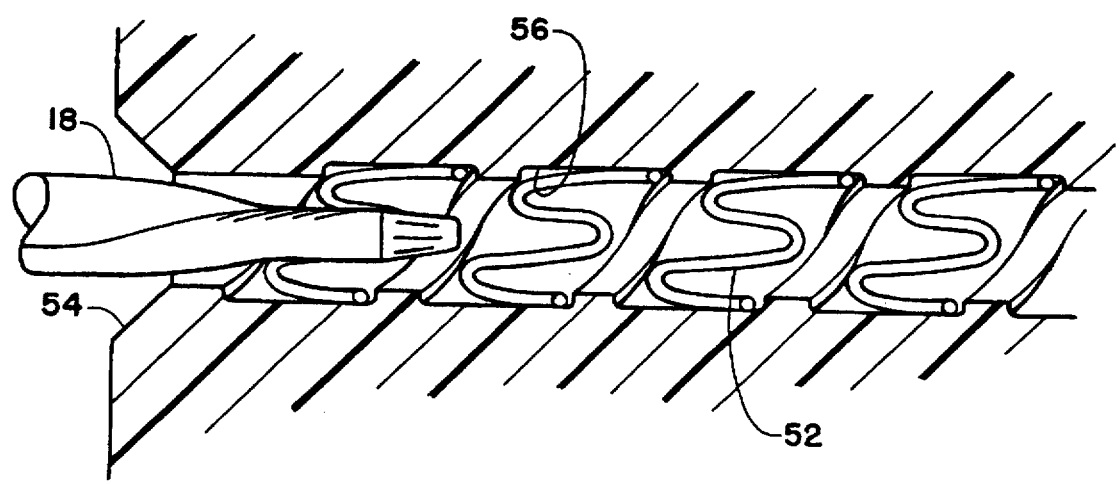
FIGURE 5

STENT MOUNTING DEVICE

FIELD OF THE INVENTION

This invention relates in general to intervascular stent implants for maintaining vascular patency in humans and animals and more particularly to a method and apparatus for supporting a stent and for transferring the stent to a delivery system such as a balloon catheter.

BACKGROUND OF THE INVENTION

Percutaneous transluminal coronary angioplasty (PTCA) is used to reduce arterial build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from the small coronary vessels to the 30 mm aortic vessel. The invention applies to acute and chronic closure or reclosure of body lumens.

A stent typically is a cylindrically shaped device formed from wires or a slotted tube and intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

The metal stent that props open blocked coronary arteries, keeps them from reclosing after balloon angioplasty. A balloon of appropriate size and pressure is first used to open the lesion. The process is repeated with a stent crimped on a balloon. The stent is deployed when the balloon is inflated. The stent remains as a permanent scaffold after the balloon is withdrawn.

A number of different stent structures and placement instruments have been developed. For example, Wall in U.S. Pat. No. 5,266,073 describes a rolled tubular stent carried at the end of a tubular catheter with a second catheter threaded therethrough to carry a balloon. The assembly is inserted into an artery until the stent is at the proper location, then the balloon catheter is positioned within the stent and expanded to expand, unroll and lock the stent. This arrangement usually requires an undesirably large diameter catheter for carrying the stent and includes a complex and possibly unreliable locking method for holding the stent in the expanded position. Also, non-uniform stent expansion may occur, since the expanding balloon cannot directly contact the portion of the stent that overlaps its carrier catheter.

Other stent delivery systems have a self-expanding stent compressed in a tube, such as that described by Burton et al. in U.S. Pat. No. 5,026,377. The tube is inserted until the stent is in the desired location and the stent is forced from the tube and expands into contact with the vessel wall. A balloon catheter may be inserted and expanded to further expand the stent. Problems may arise with maintaining the partially expanded stent in position and preventing pushing the stent out of position during insertion of the balloon catheter.

Others have used a rolled tubular stent placed around a balloon catheter and covered by a tubular sheath connected to a guidewire extending through the catheter, such as is described by Lau et al. in U.S. Pat. No. 5,158,548. The assembly is inserted into a desired location in a body lumen, the sheath is moved longitudinally by the guidewire away from the stent and the balloon is expanded to expand the stent. This requires a complex tubular catheter, sheath and stent assembly.

Balloon catheters are available with a stent preloaded around the balloon. This requires a second balloon catheter to be used to dilate the lesion enough to allow the stent to enter. Subsequently, the catheter bearing the stent is introduced and the stent emplaced. This requires the use of two expensive catheters to complete placement of the stent and two catheterization.

Loose stents are available which users simply slip over a balloon catheter and crimp against the catheter balloon with the fingers. While this arrangement is simple and quick, the stent may be damaged during storage and handling prior to use, while it is being placed over the catheter balloon or during the crimping step. Damaged stents cannot be used. If damage to the stent is not noticed, the stent may not perform as intended in use. Further, depending on the type of delivery system, fitting the stent over the delivery end without damage is sometimes difficult.

Excellent methods and apparatus for mounting stents on catheter balloons and the like are described by Rupp et al. in U.S. patent application Ser. No. 08/576,720, filed Dec. 21, 1995 and assigned to the assignee of this application. While the methods and apparatus described in that application provide excellent results, I have found that in some instances a disposable mounting device is preferable.

Thus, there is a continuing need for improved devices and methods for mounting a stent onto a delivery system such as a balloon catheter that are simpler, less expensive, more convenient, more reliable, avoid damage to the stent and include a sterile, disposable, mounting device to avoid contact between a sterile stent and catheter and a non-sterile surface.

SUMMARY OF THE INVENTION

The above-noted problems, and others, are overcome in accordance with this invention by a stent mounting device and method of using the device comprising a disposable device for holding a stent, into which a delivery system such as a balloon catheter can be inserted, then simply squeezing the device from opposite sides crimps the stent onto the delivery system, after which the delivery system and mounted stent are removed from the device.

A stent is carried in a channel formed by four corner segments of four concentrically spaced blocks. Two adjacent blocks are elastically mounted in each of two parallel, opposed cooperating actuators. The corner segments form an elongated channel sized and shaped to retain a stent of the type generally referred to as a Wiktor or Wiktor-I stent or other Medtronic Stents. Opposite ends of the two actuators are secured to elastic end members which permit the actuators to be manually moved toward each other. End caps are secured over the end members and include guides that guide the two actuators toward and away from each other along substantially straight lines.

Holes are provided through the end caps and end members in alignment with the channel so that a catheter or the like can be inserted into the channel to align with the stent carried by the channel.

Elastic rods are provided between the actuators along lines parallel to the channel. The elastic mounts for the blocks are configured so that when a delivery system is inside the stent, as the actuators are manually pressed together initially the channel is narrowed along the axis of applied pressure, then the elastic rods press the blocks toward the channel transverse to the axis of applied pressure, to narrow the channel in that direction. The stent is thus uniformly and smoothly pressed against the delivery system and crimped thereagainst. When pressure is released on the actuators, the channel expands in accordance with the elasticity of the rods and blocks to essentially the original diameter. The delivery system with mounted stent is then removed.

The components of this device can be economically manufactured by injection molding, or other equivalent method, and can be easily bonded together by adhesive, ultrasonic, heat or other suitable bonding method. For optimum assembly, cooperating pins and recesses are provided between components to aid in alignment and bonding. Preferably, the device is formed from a flexible transparent plastic material such as a suitable acrylic resin, allowing easy observation of the stent, delivery system and alignment before pressing to crimp the stent. Since the manufacturing methods and materials are inexpensive, the device can be supplied within sterile condition with a stent in place, then can be disposed of after a single use.

In present practice, two "delivery" systems such as balloon catheters are required for implanting a stent for procedures such as percutaneous transluminal coronary angioplasty. Typically, a first delivery system, such as a balloon catheter is inserted and the balloon expanded to press a lesion outwardly and make room for a stent. A balloon catheter, preloaded with a stent, is inserted and the stent is moved to the desired location and the balloon is expanded to expand the stent against the vessel wall. With the device of this invention only a single balloon catheter delivery system is required. A catheter balloon can be rewrapped after the first expansion step. The catheter balloon is then inserted into the device and a stent is crimped onto the balloon with the device. The stent can be emplaced as before.

It is, therefore, an object of this invention to provide an improved device and method for placing stents onto any of a variety of delivery systems, such as wrapped balloon catheters. Another object of the invention is to reduce or prevent damage to stents during placement onto delivery systems. A further object is to provide a device for mechanically applying a stent to a delivery system which does not require manual finger crimping of the stent. Yet another object is to provide an arrangement in which a single balloon catheter can be used to dilate a lesion and place a stent at the lesion site. Other objects and advantages of the stent installation device and method of this invention will become apparent upon reading the following description of preferred embodiments.

BRIEF DESCRIPTION OF THE DRAWING

Details of the invention, and of preferred embodiments thereof, will be further understood upon reference to the drawing, wherein:

FIG. 3 is a section view taken on line 3—3 in FIG. 1 prior to compressing the device;

FIG. 4 is a section view taken on line 3—3 in FIG. 1 subsequent to compressing the device; and FIG. 5 is a section view taken on line 5—5 in FIG. 1.

DETAILED DESCRIPTION OF PREFERRED EMBODIMENTS

Figure 1:
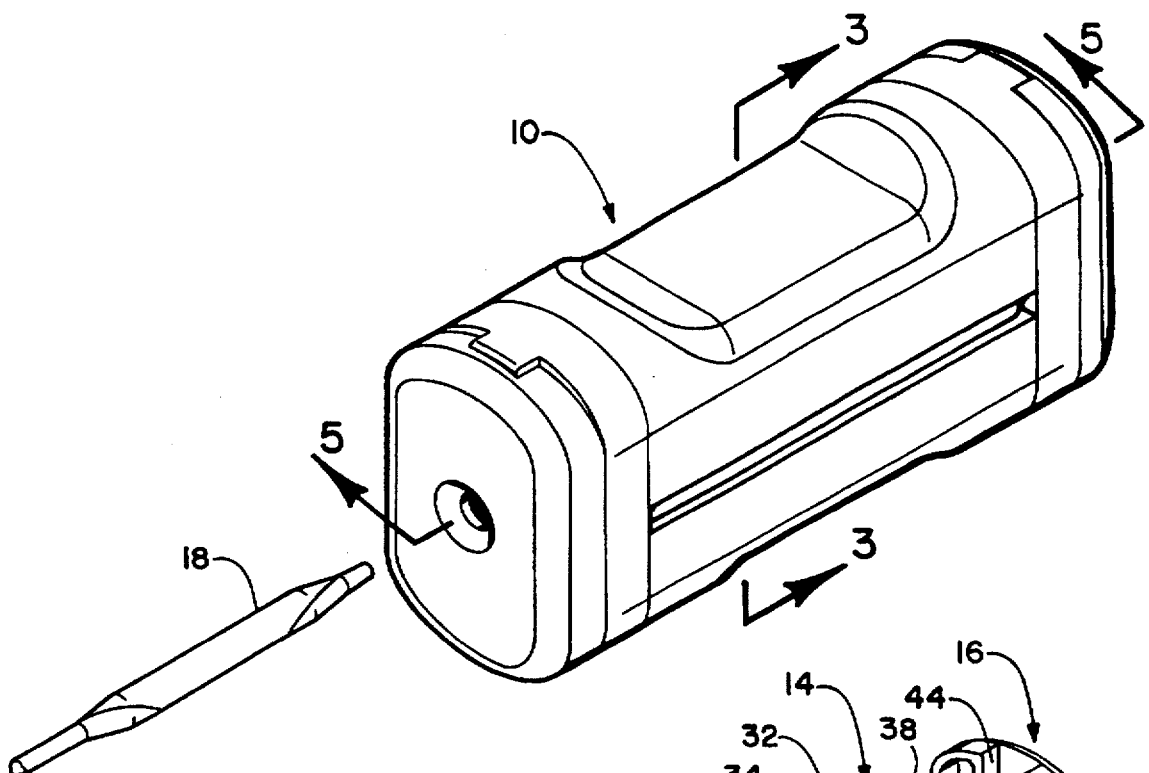
FIG. 1 is a perspective view of the stent installation device of this invention and a wrapped balloon upon which a stent is to be installed.
Figure 2:
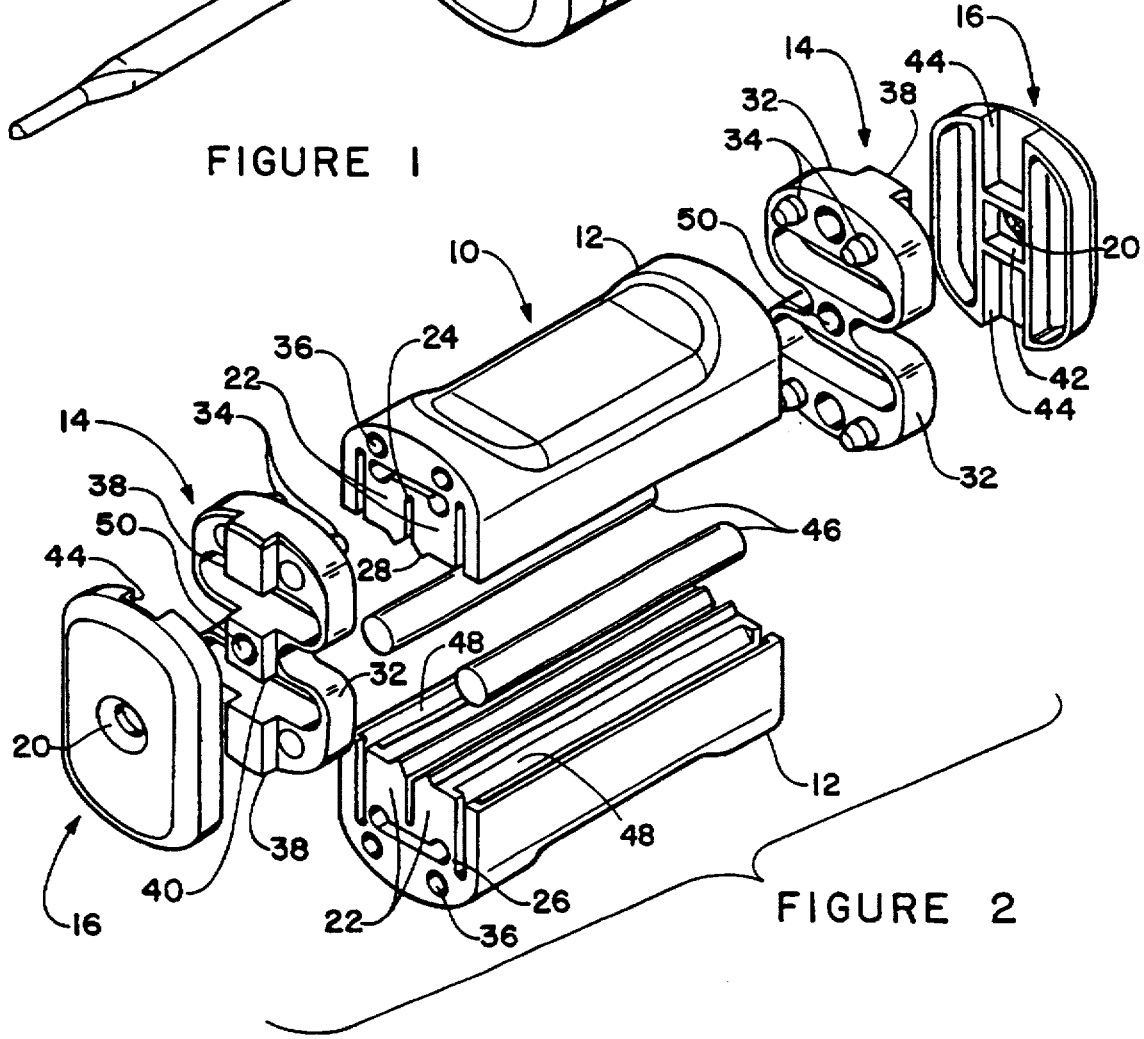
FIG. 2 is an exploded view of the stent installation device.

Referring to FIGS. 1 and 2, there is seen a device 10 having two generally identical actuator pieces 12, two elastic guide members 14 and two end caps 16. A stent delivery system, such as the balloon catheter 18, with the balloon wrapped, as seen in FIG. 1, can be inserted into device 10 through hole 20.

Within each of actuators 12 are formed a pair longitudinal blocks 22, as best seen in FIGS. 2–4. Each pair of blocks is secured together by a thin web 24 and to the interior of actuator 12 by thin webs 26. Actuators 12 are preferably formed from a resilient material so that, together with the thin webs 24 and 26, the positions of blocks 22 can be changed with relatively little force. Each block 22 has a corner segment 28 which formes a portion of a central channel between the four segments 28.

Guide members 14 have ends 32 which carry pairs of pegs 34 which tightly fit in recesses 36 in actuators 12. Pegs 34 are bonded in recesses 36 in any suitable manner, such as by an adhesive, ultrasonic bonding, thermal bonding, etc. No other part of guide members 14 are bonded to actuators 12.

Each guide member 14 has three outward protuberances, two sliding protuberances 38. The inner surface of each end cap 16 includes a central recess 42 which fits tightly over central protuberance 40 and is bonded thereto by an adhesive, etc. Sliding protuberances 38 fit in elongated recesses 44 and are slidable therein along a straight line. End caps 16 are bonded to guide members 14 only at central protuberance 40.

A pair of elongated elastic rods 46 are positioned in a cooperating shallow groove formed at the intersection of each opposed surface of actuators 12 and slots 48 between the exterior housing of actuators 12 and blocks 22. With endcaps 16 and guide members 14 in place on actuators 12, rods 46 are held in place with light elastic pressure. Central channel 30 is open to the maximum cross sectional area. While channel 30 preferably has a general circular cross section, other shapes could be used if desired to accommodate other stent cross sections. Channel 30 is open at both ends through holes 50 in guide members 14 and end caps 16.

A stent 52, as seen in FIG. 5, is placed in channel 30 during assembly of the device and is held in place by very light contact of the corner segments 28 thereagainst. As schematically illustrated in FIG. 5, a stent 52 is positioned in channel 30, which may have a slightly tapered entrance section 54. Where a banded stent 52, of the sort generally known as a "Wiktor" stent is used, the interior wall of channel 30 (formed by corner segments 28), can be molded with a complementary series of shallow recesses 56 to further hold the stent in place.

When a delivery system, such as the balloon catheter 18 is inserted into channel 30, the device is in the configuration shown in FIG. 3. The stent 52 and channel 30 are sized to easily receive the selected delivery system 18. Where the device is transparent, the position of the stent and delivery system can be easily observed through he device. Once delivery system 18 is in the desired position, the two actuators 12 can be manually pressed toward each other with the fingers. As actuators 12 move together, sliding protuberances 38 move together in elongated recesses 44 and elastic rods 46 are compressed along the line of pressure and enlarge in a direction transverse to the line of pressure, as seen in FIG. 4. Thus, channel 30 is uniformly reduced in cross sectional area, both as the space between blocks 22 in opposite actuators 12 decreases and as rods 46 force blocks 22 together in the transverse direction. When the corner segments 28 come fully together, the channel has been reduced in size sufficiently to properly crimp stent 52 around delivery system 18. The squeezing pressure on actuators 12 is released and elastic forces in the rods 46, blocks 22 and guide members 14 combine to return the device to the configuration shown in FIG. 3. Delivery system 18, with stent 52 crimped in place is removed for use.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. A device for crimping a stent onto a catheter delivery system which comprises:

a generally tubular channel having a longitudinal axis and having a circumferential wall formed by four spaced longitudinal segments of four spaced blocks;

retention means along said generally tubular channel for retaining a stent against said circumferential wall;

entrance means at an end of said generally tubular channel for allowing a delivery system to be inserted into said generally tubular channel and be positioned at a predetermined position relative to said retention means;

pressure application means for forcing said four spaced longitudinal segments toward said longitudinal axis to compress and crimp said stent against said delivery system to form a unitary delivery system and stent assembly; and elastic means engaging said four blocks for releasing said compression and expanding said channel to allow said delivery system and stent assembly to be removed from said channel through said entrance means.

2. The device according to claim 1 wherein each of said four spaced longitudinal segments is formed at a corner of one of four circumferentially spaced blocks.

3. The device according to claim 2 wherein said pressure application means comprises two opposed actuators movable towards each other in a pressure application direction, each actuator elastically supporting adjacent pairs of said circumferentially spaced blocks.

4. The device according to claim 3 further including elastic rod means mounted substantially parallel to said generally tubular channel between said blocks on said opposed actuators so that when said opposed actuators are moved together, said rods are compressed and rod thickness is decreased in the direction of pressure application and rod thickness is increased in a transverse direction, for moving said blocks to compress said generally tubular channel in said pressure application direction and said rod transverse thickness increase moves said blocks to compress said channel transverse to said pressure application direction.

5. The device according to claim 1 wherein said retention means comprises shallow recesses in said circumferential wall configured to receive said stent therein.

6. The device according to claim 1 wherein said pressure application means comprises two spaced actuators having ends, said elastic means comprises elastic guide means secured to said ends of said spaced actuators and further including end caps fastened to said elastic guide means opposite said spaced actuators for guiding said actuators for movement toward and away from each other along substantially straight lines.

7. The device according to claim 1 wherein said device is made up of components at least one of which is formed from transparent plastic materials so that said stent and delivery system may be observed through said device.

8. A device for installing a stent on a catheter which comprises:

a substantially straight generally cylindrical channel having a central axis and a channel wall formed by four spaced corner segments of four concentrically spaced blocks;

recesses in said channel wall configured to retain a stent;

two adjacent said blocks elastically mounted on each of first and second actuator members having ends;

two elastically deformable guide members elastically secured to ends of said first and second actuator members to permit said first and second actuator members to be manually moved toward each other;

an end cap secured to each said guide member, each end cap including means for guiding guide member deformation and said first and second actuator member movement toward each other along substantially straight lines;

elastic rod members between said first and second actuator members adjacent to said channel in operative engagement with said blocks;

whereby movement of said first and second actuator members toward each other moves said block segments together along a line of pressure application and said rod members move said block segments together along a line transverse to said line of pressure application to crimp a stent in said channel around a catheter placed within said stent in said channel.

9. The device according to claim 8 wherein each of said two adjacent blocks are joined to said actuator by a first web and together by a second web, each of said webs extending substantially parallel to said channel axis.

10. The device according to claim 8 wherein said device is made up of components at least one of which is formed from transparent plastic materials so that of said stent and delivery system may be observed through said device.

11. The device according to claim 8 further including a hole through each of said guide members and end caps coaxial with said channel.

12. The device according to claim 8 wherein said actuators, guide members and end cap include cooperating pegs and recesses for bonding together for forming a unitary structure.

\* \* \* \* \*

UNITED STATES PATENT AND TRADEMARK OFFICE
CERTIFICATE OF CORRECTION

PATENT NO. : 5,672,169
DATED : September 30, 1997
INVENTOR(S) : Marcel A.E. Verbeek It is certified that error appears in the above-identified patent and that said Letters Patent is hereby corrected as shown below:

Col. 2, Line 33:     "beating"     should be     "bearing"

Signed and Sealed this

Seventeenth Day of February, 1998

Attest:

BRUCE LEHMAN

Attesting Officer      Commissioner of Patents and Trademarks